United States Patent

Tamminmäki et al.

Patent Number: 5,562,704
Date of Patent: Oct. 8, 1996

[54] SURGICAL IMPLANT

[75] Inventors: Markku Tamminmäki, Tampere, Finland; Gert Kristensen, Ebeltoft; Peter Albrecht-Olsen, Charlottenlund, both of Denmark; Pertti Törmäälä, Tampere, Finland

[73] Assignee: Biocon Oy, Tampere, Finland

[21] Appl. No.: 256,808

[22] PCT Filed: Jan. 18, 1993

[86] PCT No.: PCT/FI93/00014

§ 371 Date: Oct. 3, 1994

§ 102(e) Date: Oct. 3, 1994

[87] PCT Pub. No.: WO93/14705

PCT Pub. Date: Aug. 5, 1993

[30] Foreign Application Priority Data

Jan. 24, 1992 [FI] Finland .................................. 920305

[51] Int. Cl.⁶ .................................................. A61B 17/00
[52] U.S. Cl. ........................... 606/213; 606/67; 606/75; 606/151
[58] Field of Search ................................. 606/213, 215, 606/151, 221, 219, 62, 67, 72, 75, 232; 411/923, 500, 508–510

[56] References Cited

U.S. PATENT DOCUMENTS 4,873,976  10/1989  Schreiber .
5,425,747   6/1995  Brotz ........................................ 606/215

*Primary Examiner*—Michael Powell Buiz
*Assistant Examiner*—Jeffrey A. Schmidt
*Attorney, Agent, or Firm*—Pollock, Vande Sande & Priddy

[57] ABSTRACT

The present invention relates to a surgical implant made of a polymer or a polymeric compound which is substantially absorbable in tissue and contains reinforcing structures made of a polymer or a polymeric compound. The implant has a body with a first end formed as a stem and a second end formed as a head. The implant also contains arresting members for arresting the implant in a position in a direction opposite to the direction of installation. The stem protrudes from the outer surface of the body and substantially formed of at least one wing extending in the longitudinal direction of the body. The wing is connected to the body at one edge. The body contains a plurality of cuts adjacent the head which define the arresting members and are formed in a direction substantially parallel to the body.

20 Claims, 2 Drawing Sheets

SURGICAL IMPLANT

FIELD OF THE INVENTION

The present invention relates to a surgical implant formed in the shape of an arrow comprising a body whose first end is formed as a stem and whose second end is formed as a head with arresting means intended for arresting the implant in a position according to the use of the implant particularly in a direction opposite to the direction of installation, wherein the stem protrudes from the outer surface of the body and wherein the implant is manufactured of a polymer or a polymeric compound which is substantially absorbable in tissue conditions and contains reinforcing structure or the like, also of a polymer or a polymeric compound.

The surgical implant of the invention is particularly but not solely intended to be used in repair surgery of traumas of soft and/or tough tissues containing fibrous structures, such as meniscal tissues.

BACKGROUND ART

With reference to the prior art in the field it has been shown that fixation of meniscus trausmas like ruptures and lesions by suturing with absorbable sutures gives better results than the removal of traumatized meniscal tissue (see e.g. N. A. Palmeri, T. F. Winters, A. E. Joiner and T. Evans, "The Development and Testing of the Arthroscopic Meniscal Staple", *Arthroscopy*, Vol. 5, No. 2, 1989, p. 156 (Ref. 1)). However, arthroscopic suturing is a complicated technique where risks for the patient are significant because of danger to vessels and nerves. Therefore, the desire of surgeons has been already for a long time to have an absorbable meniscus lesion fixation device like a staple or fastener which should have the advantages of absorbable suturing techniques but which could be more rapidly used and without complications of suture technique.

Several research groups have tried to develop absorbable meniscus lesion fixation devices like clamps or the like. However, the various demands upon such a device are high. It must be strong enough to maintain the good contact of lesion tissues after operation so that rapid healing occurs. The device must retain its strength long enough for good healing. It must be biocompatible and it must be absorbed without causing complications which should prevent the healing of lesion. Additionally, the installation of the device should be easy and rapid and should cause minimum operational trauma. Because of those high demands, a satisfactory, absorbable meniscus lesion fixation device has not been developed yet. Palmeri et al. reported in Ref. 1 the development of a method of meniscal repair using arthroscopically applied absorbable fasteners. However, the reported method was complicated because the final design used cannulation of the staple for needle-guided placement. Additionally staple fracture, migration and articular abrasion was found.

With regard to implants known in this field, reference is made to U.S. Pat. No. 4,873,976 which discloses an arrow-like implant particularly for repair surgery of meniscal rupture. However, the arrow-like implant according to this publication has the disadvantage that particularly its stem is shaped as a plate in a way that the direction of the main plane of the plate is perpendicular to the longitudinal direction of the body. Because of this fact, it is particularly difficult to install the implant, because the installation channel to be used in connection with installing the implant must be formed to have the cross-sectional shape of the stem; it is difficult to guide the implant in the installation channel, because the guiding effect is substantially brought upon the stem only. Furthermore, due to the structure of the stem, it causes mechanical irritation and abrasion of the tissue particularly when placed in connection with the meniscus, because the stem is usually left protruding to a high degree from the outer surface of the meniscus.

SUMMARY OF THE INVENTION

In this invention, it has been unexpectedly found that by designing a surgical implant of the invention mainly by forming the stem substantially of at least one wing or the like extending in the longitudinal direction of the body, which is at one edge connected to the body, and preferably by forming the arresting means at least partially by machining the material, for example, by cutting the material of the body in a direction substantially parallel and/or diagonal to the body, an implant is obtained which is effective during the installation in connection with a surgical operation and causes little tissue irritation in the soft and/or tough tissue after the installation. Particularly but not solely in the surgical treatment of ruptures or other damage of the meniscus, the placement of the stem essentially in the longitudinal direction of the body provides the advantage that although part of the stem remains at the surface of the meniscus when the implant is installed, the wing is placed substantially in the direction of the meniscus, whereby there is very little tissue irritation by protruding parts. Another advantage is provided by the fact that the stem is arranged substantially in the longitudinal direction of the body and preferably also has a maximum thickness equal to the diameter of the body in the direction of the thickness, namely that the installation channel of the installation instrument can be shaped so that the implant receives its guidance during the installation stage of the surgical operation on all the length of the body. The surgeon can thus install the implant with maximum security so that it is placed in the position intended for it in the right direction.

BRIEF DESCRIPTION OF THE DRAWINGS

The present invention will be more fully described in the following description with reference to the appended drawings. In the drawings.

DETAILED DESCRIPTION OF THE PREFERRED EMBODIMENTS

The implants according to the invention are manufactured of polymeric self-reinforced absorbable composites (SRAC) which have been described in several publications, including U.S. Pat. No. 4,743,257 and Finnish Pat. Appl. No. 870111. The bone fracture fixation devices manufactured of polymeric SRAC have been known earlier. However, in the meniscal repair surgery, the SRAC materials have not been previously known. Here the inventors have unexpectedly found that regardless of the totally different nature of meniscal tissue (fibrous, soft, tough and elastic) in comparison with bone tissue (hard and brittle), the meniscal repair devices made of SRAC provide good fixation of meniscal lesions. Additionally, SRAC meniscal fixation devices are rapid and safe to use with a special instrument related to this invention and described in a parallel application, which is of significant benefit for surgical practice.

Polymeric SRAC is the ideal raw material in manufacturing of devices of this invention because of several reasons:

— meniscal lesion fixation devices made of SRAC are strong, tough and stiff structures so that they can be triggered with a special instrument to penetrate into the meniscal tissue, traverse the rupture or lesion and penetrate also to the meniscal tissue on the other side of rupture or lesion without the need to use some kind of auxiliary guides like needles, cannulated tubes like in the earlier known techniques, — the strong SRAC devices maintain the ruptured meniscal parts in contact with each other during the early period of healing leading to a rapid consolidation of the lesion or rupture in the tissue, and — the absorption of SRAC implant guarantees that after absorption there is no risk of implant related long term complications, such as inflammatory reactions or infections which may occur with biostable polymeric implants even years after operation.

Partially crystalline, absorbable polymers, copolymers or polymer mixtures or alloys are especially suitable raw materials for manufacturing of the implant of this invention. Some suitable polymers that can be used as materials for the implant include polymers known from the following publications:

U.S. Pat. No. 4,700,704; U.S. Pat. No. 4,653,497, U.S. Pat. No. 4,649,921; U.S. Pat. No. 4,559,945, U.S. Pat. No. 4,532,928; U.S. Pat. No. 4,605,730, U.S. Pat. No. 4,441,496; U.S. Pat. No. 4,435,590.

The implants of the invention can be manufactured of the above polymers by applying either one polymer or a suitable polymer alloy or mixture.

Figure 1:
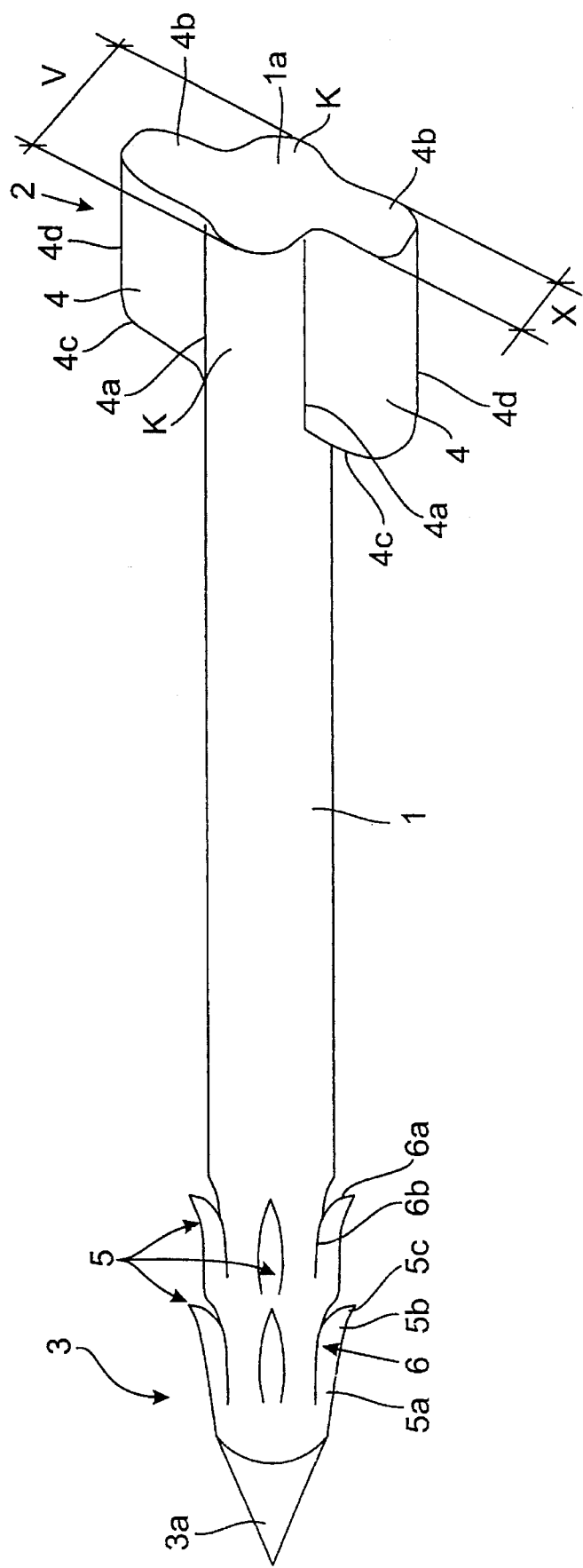
FIG. 1 shows a perspective view of an embodiment of the surgical implant according to the invention.
Figure 2:
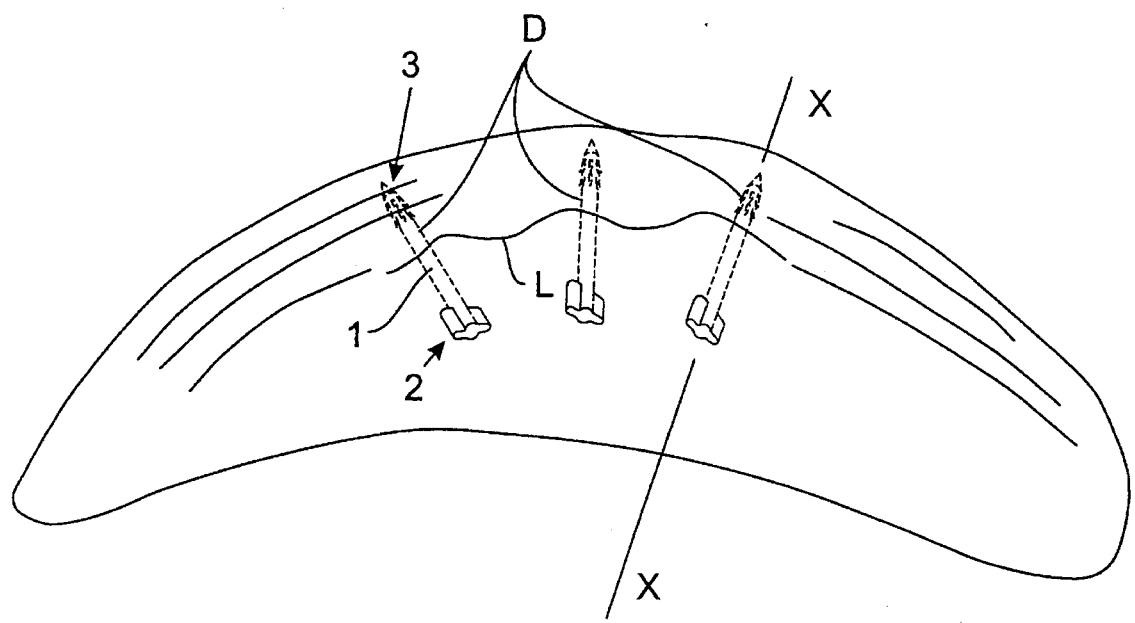
FIGS. 2–5 show sectional views of the meniscus, in which one or several surgical implants according to the invention have been installed.

FIG. 1 shows a typical surgical implant according to the invention. It is designed to have an arrow shape, and it comprises a body 1 whose one end is formed as a stem 2 and whose other end is formed as a head 3. The head comprises arresting means 5 extending at a section of the body 1. The purpose of the stem 2 is to stop the implant at the final stage of the installation and to prevent the implant from moving in the direction of installation when it is already in the installed position. The arresting means 5 are intended to keep the implant installed in the position of use, particularly in the direction opposite to the direction of installation. Thus, the stem 2 protrudes from the outer surface of the body 1 firstly for the purpose of arresting as described above, and secondly for the purpose of providing the impact surface required for the instrument used in the installation of the implant.

According to the invention, the stem 2 is formed of at least one wing or the like 4 extending substantially in the longitudinal direction of the body 1. Each wing 4 connected with the stem 2 is at one edge 4a attached to the outer surface of the body 1. Further, the other edge surface 4b of the wing, attached to the edge 4a in perpendicular direction, is designed to be parallel with the back surface 1a of the body 1. This back edge surface 4b of the wing is situated essentially in the same plane as the back surface 1a of the body 1 to form the wide impact surface required for the front surface of the instrument. The thickness of the wing 4 or the like, i.e. the dimension x does not exceed the maximum dimension V of the body 1 in the direction of dimension x.

In the embodiment shown in FIG. 1, the implant comprises two wings 4 protruding from the body 1 at the stem 2 in two directions. In the embodiment shown in FIG. 1, the parts protrude radially in opposite directions as seen in the longitudinal direction of the body, whereby the wings 4 form an integrated plate-like piece having a bulge K at its center formed by the outer surface of body 1 on both sides of the main plane of the plate-like piece.

As shown in FIG. 1, each wing 4 has a substantially quadrangular form, preferably a rectangular or trapezoid form, whereby in the direction of installation of the wing 4, the third edge 4c is substantially transverse or perpendicular to the longitudinal direction of the body 1 and thus provides an effective arresting impact at the end of the installation operation and keeps the implant in its position.

The body 1 can have a polygonal or curved cross-section, but in an advantageous embodiment, the cross-sectional form of the body is a circle with a substantially even thickness, as shown in FIG. 1. The thickness x of the wing can thus be smaller than the diameter V of the circular form. The dimension x of the wing can have an even thickness or it can taper off or widen from the first edge 4a towards the fourth and outermost edge 4d of the wing 4.

The arresting means 5 which, particularly in combination with the sharp end 3a of the head 3, are formed in such a manner that they do not completely protrude from the outer surface of the body 1. This facilitates the installation of the implant first as it moves in the installation channel of the instrument and further as it penetrates the tissue. The arresting means 5 are formed as a kind of scutellate structure, for example, in two (or more) subsequent lines or mixed formations at certain distances on the whole perimeter of the body as shown in FIG. 1. The arresting means 5 adjacent with the head 3 are formed by cuts 6 or the like made in the polymer material of the body 1. The cuts separate part of the material of the body 1 to form barbs or the like, their base parts 5a being connected to the body 1 and their bodies 5b and heads 5c being directed to the stem 2 of the implant. The cuts 6 or the like are formed toward comprise a first, substantially curved section 6a, where the head 5c of the said arresting means 5 is formed, and a second section 6b substantially parallel to the longitudinal direction of the body, where the body 5b of the arresting means 5 is formed. In the installed position of the implant, the arresting means 5 tend to be directed outwards from the body, if the implant is subjected to forces which tend to move it in the direction opposite to the direction of installation. Thus, the scutellate structure of the arresting means, positioned in two adjacent lines on the whole perimeter of the body in its longitudinal direction, prevents the movement of the stem in the direction opposite to the direction of installation. It is obvious that the cuts 6 can be formed by a cutting means also to be directed at an inclined angle inwards the body 1, whereby the material forming the arresting means 5 of the body 1, particularly its head 5c, bends to protrude from the outer surface of the body 1.

The arresting means 5 are thus at least partly formed by working, for example, cutting, the material of the body 1 substantially in the longitudinal direction of the body 1. Part of the arresting means 5 can naturally be formed for example, of structures known in U.S. Pat. No. 4,873,976.

Figure 3:
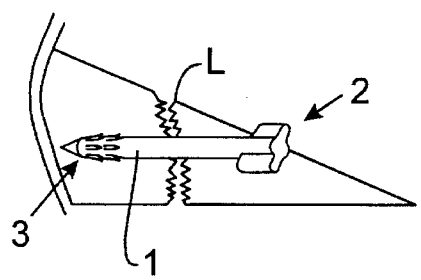
Figure 4:
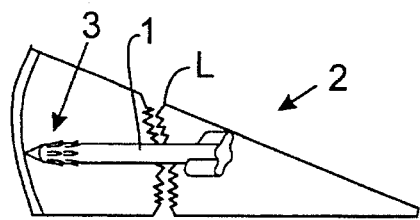
Figure 5:
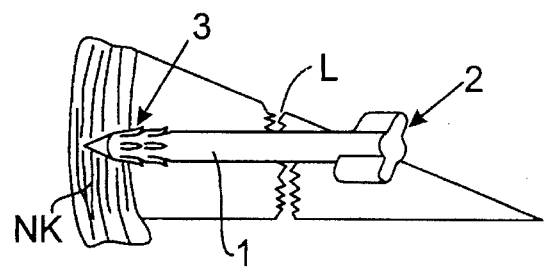

FIGS. 2–5 show schematically how three implants D of the type illustrated in FIG. 1 are used in fixation of a meniscal lesion L. The stems of the implants 2 (solid lines) are on the outer (upper) surface of the meniscus. The bodies and the heads of the implants (drawn by broken lines) are inside the meniscal tissue. FIG. 3 shows in a cross-sectional side view in vertical plane in the direction x—x of FIG. 2 how a meniscal repair implant penetrates the lesion L so that its body 1 and head 3 are inside of the meniscal tissue and the stem 2 is at least partially on the surface of the meniscus. It is possible also to trigger the implant totally inside of the meniscal tissue as shown in FIG. 4. In this case, the irritation effect of the implant inside of joint cavity is minimal. In ruptures near the joint capsule NK, the head 3 can penetrate through the meniscal tissue into the joint capsule NK as shown in FIG. 5.

The self-reinforced absorbable implants of this invention can be manufactured of absorbable polymers, copolymers or polymer mixtures or alloys with several methods. It is possible to use the techniques of U.S. Pat. No. 4,743,257 to sinter in a compression mold absorbable fibers (and possibly additional binding polymer powder) together to create a self-reinforced structure. The implants of this invention can be molded ready in a single compression molding cycle, or they can be machined at least partially mechanically (and using possible additional heat) after sintering.

The self-reinforced structure can be created also during extrusion or injection molding of absorbable polymeric melt through a suitable die or into a suitable mold at high speed and pressure. When cooling occurs at suitable conditions, the flow orientation of the melt remains in solid material as self-reinforcing structure. In an advantageous embodiment, the mold can have the form of the implant, but it is also possible to machine injection-molded or extruded semifinished products to the implants of the invention mechanically (and using possibly also heat).

The self-reinforced implants of this invention can be manufactured also by machining mechanically (and/or possibly also using heat) from self-reinforced extruded or injection-molded and drawn semifinished products, such as rods and wings described in WO 88/05312.

In some advantageous embodiments of this invention, the reinforcing elements of the self-reinforced structure are mainly oriented in the direction of the long axis of the stem of the implant. The reinforcement elements can also turn spirally around the long axis of the implant. Also other different orientations of reinforcement elements in elongated samples which are familiar from composite technology can be applied (see e.g. *Engineered Materials Handbook*, Volume 1, Composites, ASM International, Metals Park, Ohio 44073 USA, 1988). However, a general feature of self-reinforcement of the implants of this invention is that an essential part of reinforcing elements is oriented in such a way that they can carry effectively the different loads (such as tensile, bending and shear loads) which are directed to the healing meniscal tissue from the outside (for example, because of the movements of the patient's knee).

According to an advantageous embodiment of the invention, the meniscal repair implant may contain one or more bioactive substances, such as antibiotics, chemotherapeutic substances, substances accelerating the healing of the wound, growth hormones and the like. Such bioactive meniscal repair implants are especially advantageous in surgical use, because they contribute with biochemical, drug and the like, effects to the healing of the lesion in addition to the mechanical supporting effect.

The self-reinforced materials of the implants typically have tensile strengths of 100–500 MPa, bending strengths of 100–400 MPa and shear strengths 80–200 of MPa. Additionally, they are usually stiff and tough. These mechanical properties are superior to those of non-reinforced absorbable polymers which typically show strengths between 40 and 100 MPa and are additionally either very flexible or brittle (see e.g. S. Vainionpää, P. Rokkanen and P. Törmälä, "Surgical Applications of Biodegradable Polymers in Human Tissues", Progr. Polym. Sci. 14 (1989), pp. 679–716).

The implants of the present invention as well as the instruments are sterilized by any of the well known sterilization techniques generally depending on the type of material used in manufacture of the implant or the instrument or its components. Suitable sterilization techniques include heat or steam sterilization, radiation sterilization such as cobalt 60 irradiation or electron beams, ethylene oxide sterilization, and the like.

After the description above of the present invention and certain specific embodiments therein, it will be readily apparent to those skilled in the art that many variations and modifications may be made to the present invention without departing from the spirit and scope thereof. The examples below illustrate the production of implants of the invention as also the use of implants and instruments of the invention.

EXAMPLE 1

Molds were constructed for transfer molding or for compression molding (sintering) and for injection molding of meniscal repair implants with the geometry corresponding substantially to that of the device in FIG. 1. The dimensions of the manufactured implants were: the length of the arresting means 5 connected with the head 3 in two subsequent lines: about 2.0 mm; the thickness of the cylindrical body 1: 1.4 mm; the dimension x of the wing 4: 1.1 mm; the edge 4a: 3 mm and edges 4b, 4c: 1.5 mm. The total length of the implants was 15 mm. The cuts required for formation of the arresting means 5 were made at a separate stage after the compression stage.

The implants of the invention were manufactured by transfer molding in the following manner.

The melt of glycolide/lactide (90/10) copolymer (internal viscosity $|\eta|=1.5$ in 0.1% hexafluoroisopropanol solution (T=25° C.)) was mixed with 8 mm long fibers of the same material. The melt-fiber mixture was injected rapidly into the implant mold which was cooled rapidly. The fiber content of the implants was 30% (w/w). The bending strength of these self-reinforced absorbable implants was 140 MPa. The bending strength of corresponding non-reinforced devices manufactured from glycolide/lactide copolymer melt was 80 MPa.

EXAMPLE 2

The mold of Example 1 was used to manufacture implants by compression molding. Glycolide/lactide copolymer sutures (Vicryl$^R$) (size 2 USP) were heated in evacuated mold to 185° C. for about 4 min which caused the partial melting of fiber units of sutures. The material was compression molded to a device of FIG. 1a with a pressure of 2000 bar, and it was cooled rapidly. The shear strength of these self-reinforced implants was 120 MPa. The shear strength of corresponding non-reinforced devices manufactured from glycolide/lactide copolymer melt was 70 MPa.

EXAMPLE 3

The mold of Example 1 was used to manufacture the devices by compression molding. Polyglycolide sutures (Dexon$^R$) (size 2 USP) were heated in evacuated mold to 224° C. during about 5 min with a pressure of 2000 bar. The softened fiber material was fused partially together, and it filled the mold cavity shaped like the implant of FIG. 1. The mold was cooled rapidly, and the implant was removed. The tensile strength of these self-reinforced absorbable devices was 160 MPa. The tensile strength of corresponding non-reinforced implants manufactured from polyglycolide melt was 80 MPa.

EXAMPLE 4

Polyglycolide sutures (Dexon$^R$) (size 2 USP) were melted at T=230° C. The polymer melt was injected rapidly into the mold which was partially filled with continuous Dexon$^R$ sutures. The mold was cooled rapidly. The fiber content of self-reinforced implants was 40% (w/w), and their shear strength was 120 MPa. The shear strength of corresponding non-reinforced implants manufactured from polyglycolide melt was 50 MPa.

EXAMPLE 5

Isomers of absorbable polymers can be applied to manufacture implants of the invention. For example isomers of polylactide, such as poly-L-lactide (PLLA), poly-D-lactide (PDLA), poly-DL-lactide (PDLLA) and copolymers of L-lactide and D-lactide which contain different amounts of L-units and D-units can be used as such in fiber form, or mixtures of their fibers can be used to sinter the implants. PLLA is a partially crystalline polymer with a melting point of about 180° C. The isomers containing D-units have lower melting points. Therefore numerous types of self-reinforced implants can be manufactured of polylactide isomers using fibers of PLLA or of copolymer with low content of D-units as reinforcement fibers and a copolymer with higher content of D-units as matrix. The self-reinforced materials can be manufactured of these materials, for example, by combining isomer matrix and fibers, thread or corresponding reinforcement structures to each other by means of heat and pressure.

Bundles of poly-L-lactide (PLLA) fibers (fiber diameter 120 μm, molecular weight of PLLA=700,000) and the finely powdered DL isomer (molecular weight=100,000) were mixed mechanically together and compression molded in mold of Example 1 at 165° C. and 2000 bar pressure for 5 min and cooled rapidly. The fiber content of self-reinforced implants was 50%, and their bending strength was 200 MPa. Bending strengths of non-reinforced rods manufactured from polymer melts were for PLLA 600 MPa and for poly-DL-lactide 50 MPa.

EXAMPLE 6

Poly-L-lactide (Mw=700,000) fibers (diameter 100 μm) were heated in pressurized mold of Example 1 to 174° C. during for about 6 min with a pressure of 2000 bar. The softened fiber material was partially fused together filling the mold, and the mold was cooled to room temperature rapidly. The tensile strength of these self-reinforced absorbable implants was 120 MPa. The tensile strength of corresponding non-reinforced implants manufactured from poly-L-lactide melt was 50 MPa.

EXAMPLE 7

Poly-β-hydroxybutyric acid fibers (diameter 100 μm) were heated in pressurized mold of Example 1 to 175° C. for 5 min with a pressure of 2000 bar. The softened fiber material was partially fused together, and the mold was rapidly cooled to room temperature. The bending strength of these self-reinforced absorbable composite devices was 100 MPa. The bending strength of corresponding non-reinforced implants manufactured of poly-β-hydroxybutyrate acid melt was 40 MPa.

EXAMPLE 8

Polydioxanone sutures (PDS of Ethicon; size 0) were heated in pressurized mold of Example 1 to 103° C. for 6 min with a pressure of 2000 bar. The softened fiber material was partially fused together, and the mold was rapidly cooled to room temperature. The shear strength of these self-reinforced absorbable composite implants was 140 MPa. The shear strength of corresponding non-reinforced implants manufactured of polydioxanone melt was 50 MPa.

EXAMPLE 9

Glycolide/lactide (PGA/PLA) copolymer sutures (Vicryl$^R$; size 1) containing 30% (w/w) of polyglycolide sutures (Dexon$^R$; size 2) were heated in mold of Example 1 in vacuum at 180° C. for 6 min, which caused the partial melting of glycolide/lactide fiber units of Vicryl sutures. The material was compression molded to implants with a pressure of 2000 bar, and it was rapidly cooled.

A hybrid composite rod which was composed of self-reinforced glycolide/lactide material into which were embedded polyglycolide sutures was obtained. The bending strength of hybride composite material was 250 MPa. The bending strength of corresponding composite manufactured from glycolide/lactide copolymer melt reinforced with 30% (w/w) of polyglycolide sutures was 200 MPa.

EXAMPLE 10

Monofilament sutures (size 0) manufactured of polyglycolide/trimethylenecarbonate copolymer (Maxon of Davis+Geck) were heated in a pressurized mold of Example 1 to 225° C. for 4 min, applying a pressure of 2000 bar during the last 1 min. The sutures were partially fused together, and the mold was rapidly cooled to room temperature. Self-reinforced absorbable devices with the shear strength of 130 MPa were obtained. The shear strength of corresponding non-reinforced implants manufactured of totally melted Maxon sutures was 60 MPa.

EXAMPLE 11

Poly-L-lactide (PLLA; Mw=700,000) was extruded to continuous cylindrical rods with a diameter (Ø) of 4 mm. The rods were drawn to the drawing ratio 10, simultaneously raising the temperature of the rods to 90° . . . 130° C. The self-reinforced (fibrillated) structure of the drawn rods was seen microscopically.

The self-reinforced rods were cut to the length of about 20 mm and formed into the implants of the invention by attaching the stem to one end of the rod in a heated mold (T=175° C.) and by cutting a set of arresting means to the head as shown in FIG. 1.

The implants manufactured by the method described above showed bending strength of 250 MPa and shear strength of 170 MPa.

EXAMPLE 12

Polyglycolide (Mw about 50,000) was extruded to continuous rods with a diameter of 4.4 mm. The rods were drawn at 160° C. to self-reinforced rods with a diameter of 1.3 mm. The continuous rods were cut to pieces of about 21 mm, to which stems were formed in molds of Example 11 at 230° C. and arresting means were worked in connection with the head. These implants of the invention showed bending strength of 360 MPa and shear strength of 250 MPa.

EXAMPLE 13

Monofilament sutures (size 2; Maxon of Davis+Geck) manufactured of polyglycolide/trimethylenecarbonate copolymer were cut to 5–10 mm pieces and melted and extruded with a self-made piston extruder to a continuous rod with a diameter of 4.4 mm. The rod was drawn at 140° ... 195° C. to a self-reinforced rod with a diameter of 1.1 mm. The continuous, self-reinforced rod was cut to pieces of about 21 mm, and the head and stem parts were cut and formed by upsetting at T=220° C. with the method of Example 11. These devices of the invention showed shear strength of 140 MPa.

The bending strength measurements of the Examples above were made with 3-point bending by supporting the head and the stem on specially constructed supports and by bending the implant from the middle with a crosshead at a speed of 5 mm/min. The shear strength was measured from the middle of the implant with a punch tester.

The strength values were measured at room temperature (22° ... 23° C.) with a mechanical testing machine (by J.J. Lloyd Instruments, England).

EXAMPLE 14

Poly-L-lactide (Mw ca. 100,000) and poly-D-lactide (Mw about 100,000) were blended in the melt state (blending ratio 1:1) in an extruder. This alloy was extruded to a rod with a 4.4 mm diameter and solidified to a stereocomplex material which exhibited a melting point of 220° C. The rod was heat treated at 180° C. and drawn to self-reinforced rod with a diameter of 1.1 mm. The self-reinforced rod was cut to pieces of 21 mm. These were upset into the arrow-shaped implants of Example 13 at 220° C. using the molds of Example 13. These implants showed the bending strength of 280 MPa. The non-reinforced injection-molded rods showed the bending strength of 120 MPa.

EXAMPLE 15

The poly-L-lactide and poly-D-lactide blend of Example 14 was extruded to 0.8 mm thick monofilaments which were drawn to fibers with a diameter of 100 μm at 110° C. The stereocomplex fibers were sintered into the devices of the invention in a compression mold by heating them for 5 min from 23° C. to 222° C. at a pressure of 2000 bar. These self-reinforced polylactide stereocomplex implants showed the shear strength of 220 MPa. The corresponding implants manufactured by injection molding of the same poly-L-lactide and poly-D-lactide melt showed the shear strength of 95 MPa.

EXAMPLE 16

Several types of self-reinforced implants with the dimensions of the implants of Example 1 were manufactured by methods according to Examples 1–15 and triggered into cadaver meniscal tissue obtained from sheep by a method disclosed in an invention "Surgical installation instrument" parallel to the present invention (copy of the patent application is enclosed). A preliminary hole (length about 15 mm) was made into the tissue with a steel punch with a diameter of 1.2 mm at an angle of approximately 45° against the surface of the meniscus. The end of the head of the implant was carefully penetrated into the preliminary hole, and the implant was triggered to the preliminary hole in the meniscus. When testing each implant material, five parallel implants were applied. All the self-reinforced implants manufactured according to Examples 1–4, 6, 9, 11, 12 and 14 sunk well into the meniscus without breaking or bending. A total of 7 implants made according to Examples 5, 7, 8, 10 and 13 buckled or bent and did not sink properly into the meniscus. However, they did not break.

Comparative triggering tests were made with injection-molded, non-reinforced implants manufactured according to Examples 1–10. Twenty-one of the implants buckled and/or broke (depending on the raw material) during triggering.

These cadaver studies showed that the self-reinforced implants of the invention did not break during triggering them into meniscal tissue. The triggering method shown in the present application is thus suitable for them. On the contrary, many of the non-reinforced implants were broken and therefore they cannot be applied with the easy and rapid triggering method.

EXAMPLE 17

Implants of the invention according to the dimensions of Example 1 were used in experimental fixation of surgically generated meniscal lesions in sheep. The following self-reinforced (SR) implants were used: SR-PGA implants of Example 3, SR-PGA implants of Example 4, SR-PLLA implants of Example 6, SR-PGA/PLA implants of Example 9, SR-PLLA implants of Example 11, SR-PGA implants of Example 12, and polylactide-stereo-complex implants of Example 15. Two animals were operated in each case. The devices were applied through an arthrotomy under direct visualization in surgically generated meniscal lesions by triggering them with the instrument of the invention into the meniscal tissue. No fracture, buckling or unfavorable migration of implants occurred during operations. Two control animals were used where lesion was not repaired. After 12 weeks, the animals were killed and the menisci were examined. The controls showed uncontrolled healing and displacement of the meniscal tissue. Most (about 80%) of the menisci treated with devices of the invention had healed well with a fibrous healing through the lesion.

We claim:

1. A surgical implant, made of a polymer or a polymeric compound which is substantially absorbable in tissue and contains reinforcing structures made of a polymer or a polymeric compound, said implant comprising:

a body having a first end forming a stem and a second end forming a head, the stem protruding from the outer surface of the body and being substantially formed of at least one wing extending in the longitudinal direction of the body, and at its one edge connected to the body, the thickness of the wing in the direction transverse to the longitudinal direction of the body not exceeding the maximum thickness dimension of the body, and arresting means for arresting the implant in a position in a direction opposite to the direction of installation, said arresting means being defined by a plurality of cuts in the body adjacent the head, said cuts being formed in a direction substantially parallel to the body.

2. A surgical implant according to claim 1, comprising at least two wings protruding from the body in at least two directions.

3. A surgical implant according to claim 1, comprising two wings which protrude in opposite directions from the body.

4. A surgical implant according to claim 1, wherein said at least one wing has a polygonal form, and wherein the back edge surface of said wing is connected to the back surface of the body and extends in the same plane as the back surface of the body and wherein the front edge of the wing is substantially transverse to the longitudinal direction of the body.

5. A surgical implant according to claim 1, wherein the cross-sectional form of the body has substantially even dimensions in the longitudinal direction of the body.

6. A surgical implant according to claim 1, wherein the body has a circular cross-section, and wherein the thickness of the wing is smaller than the diameter of said circular cross-section.

7. A surgical implant according to claim 6, wherein said body has substantially uniform thickness in its longitudinal direction.

8. A surgical implant according to claim 7, wherein said cuts in the body defining said arresting means form a plurality of barbs connected with the body at one end, and having their heads directed towards the stem of the implant, whereby said barbs form a scutellate structure.

9. A surgical implant according to claim 8, wherein said plurality of barbs form at least one row along the periphery of the body.

10. A surgical implant according to claim 8, wherein said plurality of barbs are positioned at random adjacent said head.

11. A surgical implant according to claim 1, wherein said at least one wing has a substantially even thickness.

12. A surgical implant according to claim 1, wherein said arresting means are formed along the whole perimeter of the body adjacent said head.

13. A surgical implant according to claim 1, wherein cuts forming said arresting means comprise a first substantially curved section, at the head of said arresting means, and a second section substantially parallel to the longitudinal direction of the implant body.

14. A surgical implant according to claim 1, wherein at least some cuts of said arresting means are substantially straight cuts diagonally directed towards the inside of the body.

15. A surgical implant, made of a polymer or a polymeric compound which is substantially absorbable in tissue and contains reinforcing structures made of a polymer or a polymeric compound, said surgical implant comprising:

a body having a first end forming a stem and a second end forming a head, said stem being formed of at least one wing protruding from the outer surface of the body and at its one edge connected to the body, and arresting means for arresting the implant in a position in a direction opposite to the direction of installation, said arresting means being defined by a plurality of members adjacent the head, said plurality of members being formed in a direction substantially parallel to the body and being spaced apart from each other along the entire periphery of the body.

16. A surgical implant according to claim 15, wherein said members form at least one row along the periphery of the body.

17. A surgical implant, made of a polymer or a polymeric compound which is substantially absorbable in tissue and contains reinforcing structures made of a polymer or a polymeric compound, said surgical implant comprising:

a body having a first end forming a stem and a second end forming a head, the stem protruding from the outer surface of the body and being substantially formed of at least one wing extending in the longitudinal direction of the body, and at its one edge connected to the body, and arresting means for arresting the implant in a position in a direction opposite to the direction of installation, said arresting means being defined by a plurality of cuts in the body adjacent the head, said cuts being formed in a direction substantially parallel to the implant body and having one end connected with the implant body and an opposite free end directed towards the stem, said plurality of cuts being spaced apart along the entire periphery of the body and forming a scutellate structure.

18. A surgical implant according to claim 17, wherein said cuts form at least one row along the periphery of the body.

19. A surgical implant according to claim 17, wherein said cuts are randomly spaced along said periphery of the body.

20. A surgical implant according to claim 17, wherein said cuts at one end are integrally connected with said body and extend away from the surface of said body at the opposite, free end thereof.

* * * * *